United States Patent
Bredberg et al.

[11] Patent Number: 5,922,017
[45] Date of Patent: Jul. 13, 1999

[54] DEVICE AND METHOD FOR IMPLANTS IN OSSIFIED COCHLEAS

[75] Inventors: Goran Bredberg, Stockholm, Sweden; Ingeborg Hochmair, Axams, Austria

[73] Assignee: MED-EL Elektromedizinische Gerate GmbH, Innsbruck, Austria

[21] Appl. No.: 08/816,081

[22] Filed: Mar. 13, 1997

Related U.S. Application Data

[60] Provisional application No. 60/013,313, Mar. 13, 1996.

[51] Int. Cl.$^6$ .............................. A61N 1/04; A61N 1/05
[52] U.S. Cl. ................................ 607/137; 607/57; 623/10
[58] Field of Search .................... 607/57, 137, 56; 623/10

[56] References Cited

U.S. PATENT DOCUMENTS

| | | | |
|---|---|---|---|
| 4,261,372 | 4/1981 | Hansen et al. | 607/137 |
| 4,284,085 | 8/1981 | Hansen et al. | 607/137 |
| 4,532,930 | 8/1985 | Crosby et al. | 607/57 |
| 4,592,359 | 6/1986 | Galbraith . | |
| 4,617,913 | 10/1986 | Eddington . | |
| 4,809,712 | 3/1989 | Kuzma . | |
| 5,000,194 | 3/1991 | van den Honert et al. . | |
| 5,095,904 | 3/1992 | Seligman et al. | 607/57 |

FOREIGN PATENT DOCUMENTS

| | | |
|---|---|---|
| 0 002 226 | 6/1979 | European Pat. Off. . |
| 2 465 474 | 9/1980 | France . |
| 2823798 | 9/1979 | Germany . |
| WO 94/00088 | 1/1994 | WIPO . |

*Primary Examiner*—William E. Kamm
*Assistant Examiner*—Carl H. Layno
*Attorney, Agent, or Firm*—Bromberg & Sunstein LLP

[57] ABSTRACT

A hearing prosthesis for implantation into a subject's ossified cochlea includes a plurality of electrode carriers associated with a single receiver/stimulator, and a plurality of contact member pairs arranged at a predetermined spacing along a fraction of the length of each electrode carrier. Each contact member pair is superficially placed on the carrier and comprises a first contact member diametrically opposed to a second contact member.

9 Claims, 3 Drawing Sheets

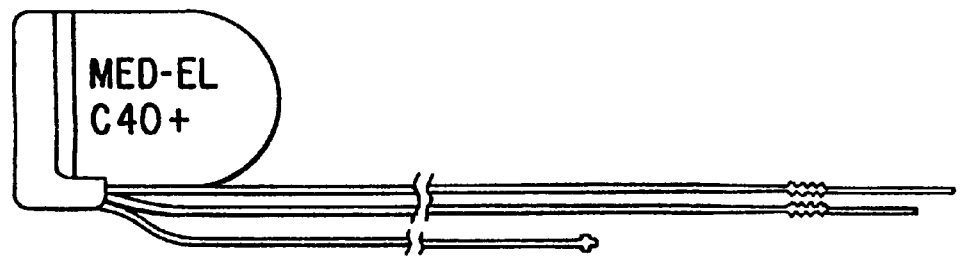
FIG. 2
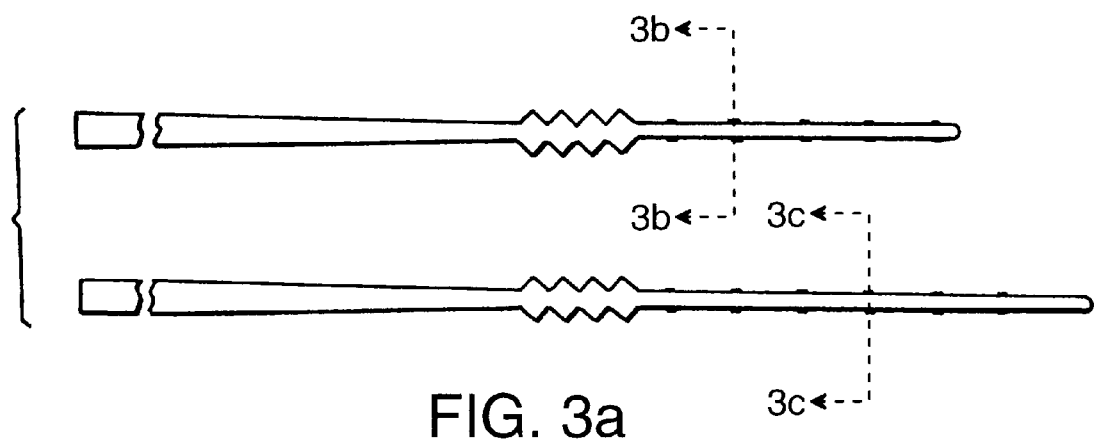
FIG. 3a
   
FIG. 3b          FIG. 3c

DEVICE AND METHOD FOR IMPLANTS IN OSSIFIED COCHLEAS

CROSS REFERENCE

This application claims the benefit of the earlier filing date of U.S. provisional patent application Ser. No. 60/013,313, filed Mar. 13, 1996 herein incorporated by reference.

TECHNICAL FIELD

The present invention relates to the structure and method of use of an implanted hearing prosthesis for use in ossified cochleas, either partly or wholly ossified cochleas.

BACKGROUND OF THE INVENTION

High performance cochlea implants have been developed, an example being shown in FIG. 1. Sound waves are received by microphone 21, sent along cables 22 to the speech processor 13, transformed into a coded signal that contains a very rapid pattern of small pulses, returned along the same cable to the transmitter 15, sent via radio transmission through the intact skin to the receiver 16, decoded and sent as a pattern of very rapid small electrical pulses to the electrodes 17 in the cochlea and delivered by the electrodes to stimulate the auditory nerve 18. Different parts of the nerve are stimulated according to the pitch of the sound waves received by the microphone. In response, the auditory nerve carries out its natural function and conducts nerve impulses to the brain. The brain receives the nerve impulses and interprets them as sound.

The step that involves delivery of electrical pulses to the auditory nerve is most effectively executed when the electrode contact is as close as possible to the auditory nerves that are particularly responsive to selected pitches of sound waves. Electrode carriers have been designed that are capable of being inserted along much of the length of the cochlea. For the Combo 40+ (Med-El), the standard distance over which the electrode pairs are arranged is 26 mm. In some patients, ossification of the cochlea has occurred such that it is not possible to insert an electrode carrier throughout the entire length of the cochlea. Therefore in these patients, the electrode carrier is shortened and the contacts are arranged over a shorter distance. (Med-El product information)

The most commonly used technique for inserting cochlear implants is to drill a bony channel corresponding to the scala tympani of the lower basal coil in a procedure referred to as a posterior tympanotomy. In ossified cochlea, the basal coil is obstructed so that it is not possible to reach all the target ganglion cells in the modiolus. Consequently the range of speech frequencies that may be registered by the patient with an ossified cochlea is reduced.

There is a need therefore for new approaches to accessing an increased number of ganglion cells in ossified cochlea.

SUMMARY OF THE INVENTION

The invention has provided a novel approach to accessing an increased number of ganglion cells in an ossified ear. In a preferred embodiment, a hearing prosthesis for implantation into a subject's ossified cochlea, is provided that includes a plurality of electrode carriers associated with a single receiver/stimulator, and a plurality of discrete shaped contact member pairs arranged at a predetermined spacing along a fraction of the length of each electrode carrier, wherein each contact member pair is superficially placed on the carrier and comprises a first contact member diametrically opposed to a second contact member.

In a further embodiment of the invention, a method of using a hearing prosthesis device for implantation into an ossified cochlea is provided that includes selecting a receiver/stimulator having a plurality of electrode carriers and implanting the electrode carriers into the cochlea such that at least one electrode carrier accesses the cochlea's lower basal coil and at least one electrode carrier accesses the cochlea's upper basal coil.

In a further embodiment of the invention a hearing prosthesis for implantation into a subject's ossified cochlea, is provided that includes a plurality of electrode carriers associated with a single receiver/stimulator; and a plurality of discrete shaped contact member pairs arranged at a predetermined spacing along a fraction of the length of each electrode carrier, such that discrete signals are transmitted to each electrode contact according to the contact's final location.

BRIEF DESCRIPTION OF THE DRAWINGS

FIG. 2 is a diagrammatic representation of the novel divided electrode carriers emerging from a MED-EL Combi 40+ receiver with a third reference electrode.

FIG. 3(a) is a scaled up view of the electrode carriers where the positions of the pairs of electrodes are marked and spacing distances provided in millimeters.

FIGS. 3(b) and 3(c) are cross-sectional views of the electrode carriers, showing the electrode contact oppositely positioned on a north and south axis such that the distance between the electrode contacts is 0.5mm and the diameter of the oval on the west-east axis is 0.6mm.

DETAILED DESCRIPTION

Figure 1:
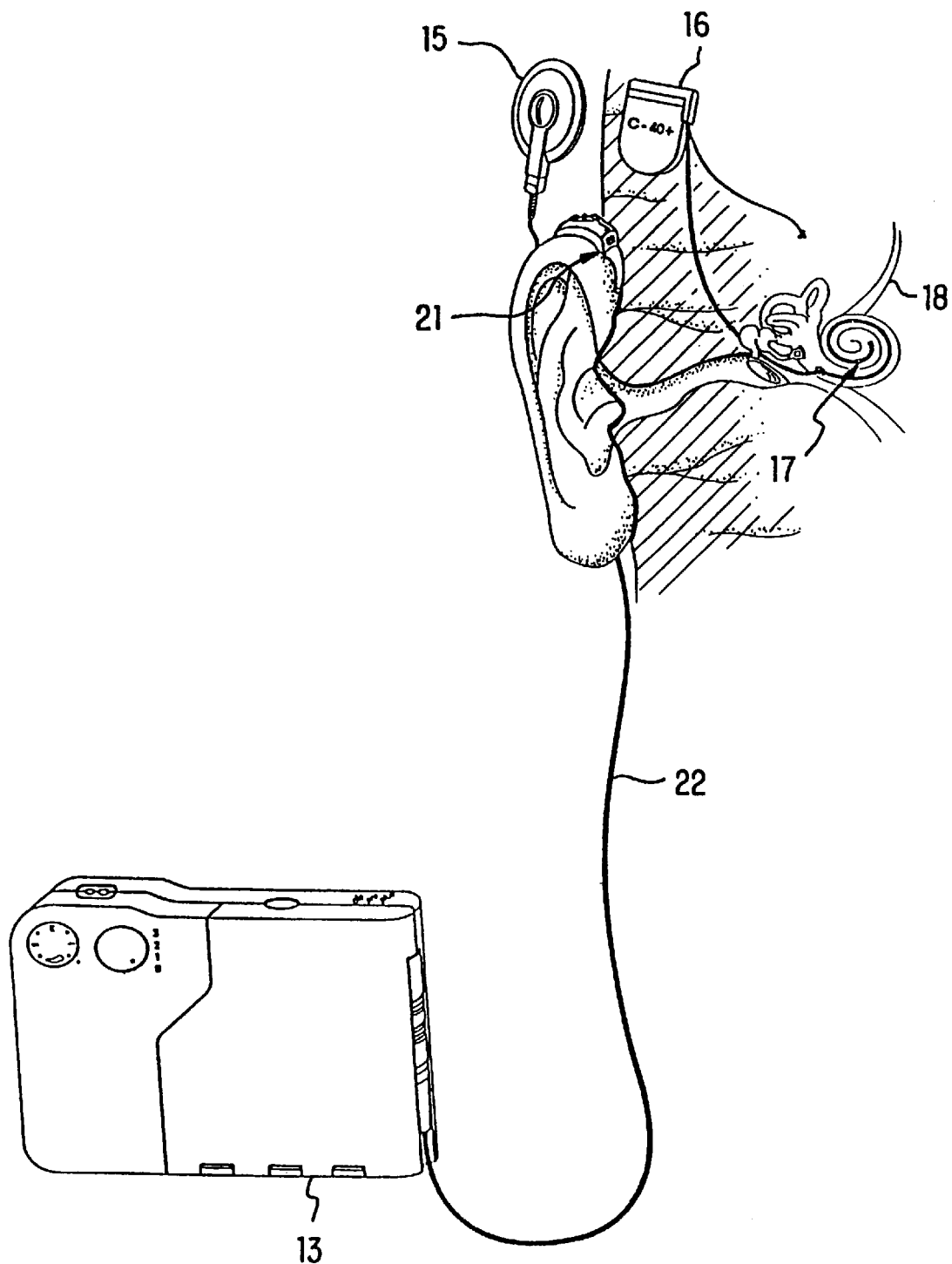
FIG. 1 is a diagrammatic representation of a Combi 40+ cochlear implant system.

The need to access an increased number of ganglion cells than is possible by means of an ossified channel has been met by using the divided electrode of the invention as exemplified in FIGS. 2 and 3(a–c) using a surgical protocol which accesses the cochlea at different sites so as to place the individual arms of the electrode carriers in different regions of the basal coil.

In an embodiment of the invention, the device includes an implantable receiver/stimulator package suitable for sending electrical pulses of different frequencies through a plurality of electrodes contained in electrode carriers that are bundled into one or more electrode carriers. Preferably a fast stimulator is used, where a fast stimulator can deliver at least 1000 pulses per second. According to an embodiment of the invention, at least one of the electrodes may be introduced through a specially drilled channel into the ossified cochlea above the site at which access is restricted. At least a second electrode is passed through the normal access point at the opening to the cochlea for accessing the non-ossified region of the cochlea.

The implantable receiver/stimulator may have a thickness of less than 4mm and may be almost completely recessed in the temporal bone. All electronic components including the receiver, and the receiver antenna are packaged in a compact heretically sealed housing. Each electrode contact has a unique electrode that emerges from the housing. The bundling of the electrodes in electrode carriers does not require a change in the electronic components within the receiver/stimulator. Instead, according to the invention, bundling of electrodes may be so organized as to be contained in a single electrode carrier or in a plurality of electrode carriers in a variety of combinations limited only by convenience to the patient and the condition of the patient's cochlea. For example, the divided electrode may consist of 2 electrode carriers containing the same or different numbers of contact members. Alternatively, the divided electrode carriers may consist of more than 2 electrode carriers, for example, 3, 4, 5 or 6 electrode carriers. The divided electrodes may contain different numbers of electrode contact pairs for example in a divided electrode carrier consisting of 2 electrode carriers, the number of contact pairs on each may differ by 2 as used in example 1, or may differ by 1,3,4,5,6,7 contact pairs or more. Some examples of combinations include 3 and 5, 5 and 7, 7 and 9, 9 and 11 contact members on a divided electrode carrier. However, in embodiments of the invention, divided electrodes may differ by as many as 10 contact pairs or more, the final design of the electrode carriers being determined according to the optimum access to the neurons in the cochlea. The signals transmitted along each electrode are selected so as to be appropriate to the position of the electrode contact in the cochlea. Thus flexibility of design provided by the arrangement where each contact has its own electrode originating from the receiver/stimulator is particularly useful in the present invention. The surgical technique for implantation of a divided electrode requires multiple access points to the cochlea, an access point being provided for each electrode carrier. Consequently, in addition to conducting a normal posterior tympanotomy, a second channel may be prepared into the cochlear in the upper basal coil. For example, access may be achieved by preparing a channel into the second turn of the cochlea, and/or into the first turn of the cochlea.

EXAMPLES

Example 1

A divided electrode suitable for insertion in a patient with an ossified cochlea.

A divided electrode was prepared as shown in FIGS. 2 and 3(a–c). A Med-El C40+ receiver/stimulator provided the source of electrical impulses communicated by 2 electrode carriers to electrode contacts adjacent to ganglia in the modiolus of the cochlea. A reference electrode was further provided as a third arm. The electrode carriers are characterized by a bundle of electrodes formed from 90% platinum and 10% iridium, a single electrode terminating at a single electrode contact (100% platinum) on the surface of the electrode carrier (formed from flexible silicone elastomer-silastic LSR 40 Applied Silicon, California) that is oval in cross section with the contacts diametrically opposed on the long axis of the oval cross section. The contacts are superficially located within a recess at the surface of the electrode. The dimensions of each of the two electrode carriers described in FIGS. 3(a–c) are as follows. For the shorter of the two electrode carriers—the contacts are evenly spaced over a 5.4mm distance, the distance between the first and the fifth contact pair being 4.4mm and the distance between a single contact pair being 1.1mm. The distance between each diametrically opposed contact in a contact pair is 0.6 mm. An intermediate section of 2 mm is located behind the region containing the contacts as a guide to the surgeon with regard to insertion. For the longer of the two electrode carriers—the contacts are evenly spaced over a 7.5 mm distance, the distance between the first and the seventh contact pair being 6.6 mm and the distance between a single contact pair being 1.1 mm. The distance between each diametrically opposed contact in a contact pair is 0.6 mm. In a preferred embodiment, the prosthesis of the present invention is made in accordance with U.S. patent application Ser. No. 08/807,038 for "Structure, Method of Use, and Method of Manufacture of an Implanted Hearing Prosthesis" filed Feb. 26, 1997 by inventors Ingeborg Hochmair and Erwin Hochmair, [bearing Attorney Docket No. 1941/109,] and claiming priority from U.S. Provisional Application for Pat. Ser. No. 60/012,261, filed Feb. 26,1996. These applications are incorporated herein by reference.

Example 2

A surgical procedure for inserting a divided electrode into an ossified cochlea.

Figure 4A:
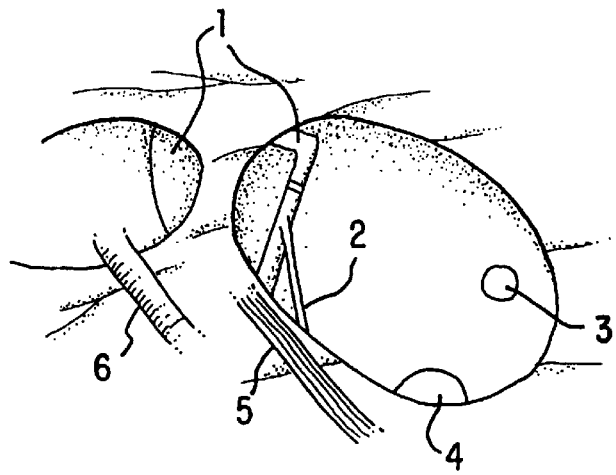
FIG. 4(a) shows a cross section of a normal posterior tympanotomy for insertion of a cochlear implant electrode carrier, showing the incus 1, the stapes 2, the cochleotomy 3, the round window 4, the facial nerve 5 and the horizontal semicircular canal 6.
Figure 4B:
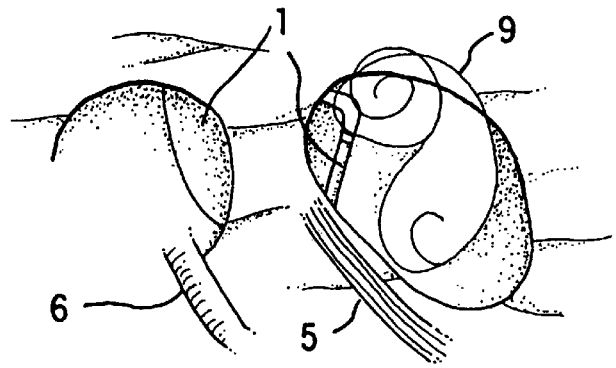
FIG. 4(b) shows the position of the cochlear fluid spaces 9 under the bone of the middle ear promontory.
Figure 4C:
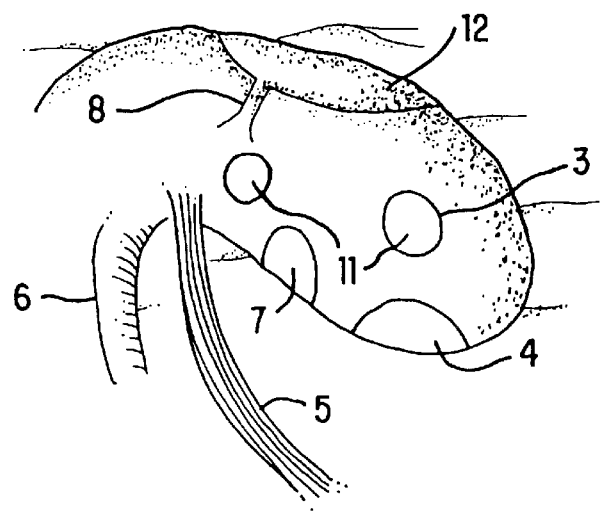
FIG. 4(c) shows a wider posterior tympanotomy which is slightly rotated suited for insertion of a divided electrode carrier. The incus is removed and the bridge of bone between the ear canal and the semicircular canal is removed. Shown in FIG. 4(c) are the malleus 12 in tympanic membrane, the posterior and anterior cochleotomy 11, the stapes footplate 7, and the tendon 8 of the tensor tympani.

An anterior cochleotomy is additionally performed in front of the round window in a manner that is standard to those ordinarily skilled in the art. Care should be taken to be located as close to the modiolus as possible. The depth of drilling is 7.5 mm. As shown in FIG. 4(a), a normal posterior tympanotomy is shown for insertion of a cochlear implant electrode. The position of the cochlear fluid spaces is shown in FIGS. 4(b) and (c). To be able to reach the upper part of the basal coil, a wider tympanotomy is performed and the bridge of bone between the ear canal and the horizontal semicircular canal is removed. The incus 1 is also removed. This exposes the middle ear with the stapes 2, facial nerve tendon 5 of musculus tensor tympani, promontory and round window 4. The crusa of the stapes are removed saving the foot plate 7. Straight in the projection of the anterior crus, a 0.8mm hole is drilled to a depth of 6.5mm. The one arm of the divided electrode that contains the five electrode pairs is used here in the region corresponding to the upper basal coil of the cochlea. The arm containing the three electrode pairs is inserted into the lower basal coil. The positioning of electrodes by means of posterior and anterior cochleotomy makes it possible to stimulate the ganglion cells in the modiolus except for one small area between the tips of the two electrodes.

In this example, the electrode carrying the greater number of contacts (the more lengthy electrode carrier) is placed in a position corresponding to the upper basal coil while the shorter electrode carrier (carrying three electrode pairs) is placed in the lower basal coil.

I claim:

1. A hearing prosthesis for implantation into a subject's ossified cochlea, comprising:
   (a) a plurality of electrode carriers associated with a single receiver/stimulator, wherein the electrode carriers have an oval cross-section the oval cross-section having a long axis, and
   (b) a plurality of discrete contact members arranged in opposing pairs along a fraction of the length of each electrode carrier.

2. A hearing prosthesis according to claim 1, wherein there is a first and a second electrode carrier associated with the single receiver/stimulator, each carrier having an odd number of pairs of electrode contact members.

3. A hearing prosthesis according to claim 2, wherein the first electrode carrier has 7 pairs of contact members and the second electrode carrier has 5 pairs of electrode contacts.

4. A hearing prosthesis according to claim 1, wherein the receiver/stimulator comprises a fast receiver/stimulator.

5. A hearing prosthesis for implantation into a subject's ossified cochlea, comprising:
   (a) a plurality of electrode carriers associated with a single receiver/stimulator, and
   (b) a plurality of contact members arranged along a fraction of the length of each electrode carrier wherein the electrode contact members are spaced at intervals of between 1 and 2 mm.

6. A hearing prosthesis for implantation into a subject's ossified cochlea, comprising:
   (a) a plurality of electrode carriers associated with a single receiver/stimulator, and
   (b) a plurality of contact members arranged along a fraction of the length of each electrode carrier wherein the electrode contact members are spaced at intervals of 1.1 mm.

7. A hearing prosthesis for implantation into a subject's ossified cochlea, comprising:
   (a) a plurality of electrode carriers associated with a single receiver/stimulator, and
   (b) a plurality of contact members arranged along a fraction of the length of each electrode carrier wherein the electrode contact members are diametrically opposed at a distance of 0.6 mm.

8. A hearing prosthesis for implantation into a subject's ossified cochlea, comprising:
   (a) a plurality of electrode carriers associated with a single receiver/stimulator, and
   (b) a plurality of discrete contact members arranged along a fraction of the length of each electrode carrier, and wherein each electrode contact member pair is superficially placed on each electrode carrier and comprises a first contact member diametrically opposed to a second contact member.

9. A hearing prosthesis according to claim 8, wherein the contact member pairs are arranged at predetermined spacing along a fraction of the length of each electrode carrier.

* * * * *